US005783736A

United States Patent [19]

Stephens et al.

[11] Patent Number: 5,783,736
[45] Date of Patent: Jul. 21, 1998

[54] PROCESS FOR AMINES

[75] Inventors: Randall Wayne Stephens, Perkasie; Renee Caroline Roemmele, Maple Glen, both of Pa.

[73] Assignee: Rohm and Haas Company, Philadelphia, Pa.

[21] Appl. No.: 938,551

[22] Filed: Sep. 26, 1997

[51] Int. Cl.$^6$ .................................................. C07C 209/08
[52] U.S. Cl. ........................................ 564/484; 564/485
[58] Field of Search ............................... 564/484, 485

[56] References Cited

U.S. PATENT DOCUMENTS 2,766,285  10/1956  Hennion .......................... 260/563
5,254,584  10/1993  Michelotti et al. .

OTHER PUBLICATIONS

Kopka, Ihor E. et al., *Preparation of a Series of Highly Hindered Secondary Amines, Including Bis(triethylcarbinyl)amine*, J. Org. Chem., 1980, 45, 4616–4622.

Hennion, G.F. et al., *The Preparation of Some Acetylenic Primary Amines*, J. Am. Chem. Soc., 75, 1953, 1653–1654.

Primary Examiner—Brian M. Burn
Attorney, Agent, or Firm—Clark R. Carpenter

[57] ABSTRACT

The process of this invention comprises a two step sequence wherein an alcohol is converted to an organic chloride through reaction with a chlorinating agent in a first step followed by amination of the organic chloride to the corresponding amine in a second step. In the second step, a surfactant is employed in order to facilitate the reaction.

22 Claims, No Drawings

PROCESS FOR AMINES

This invention relates to an improved process for the preparation of amines which are useful in the subsequent formation of biologically active materials.

The process of this invention comprises a two step sequence wherein an alcohol is converted to an organic chloride through reaction with a chlorinating agent in a first step followed by amination of the organic chloride to the corresponding amine in a second step. In the second step, a surfactant is employed in order to facilitate the reaction. The presence of the surfactant is especially valuable when the organic chloride which is formed in the first step is water insoluble but the amination agent is soluble in water. While not wanting to be bound by theory, it is believed that the surfactant increases the surface area of the organic chloride in the aqueous medium. This results in a larger contact area for reaction with the amination agent and consequently improves the mass transfer ability; thus, the time of reaction is reduced. Additionally, the selectivity and the yield of desired amine material is increased because of reduced formation of undesirable by-products; this results in an economically viable process and the ability to offer the subsequent pesticidal product to the marketplace in a more economical fashion.

The process of this invention, employing a surfactant, is most useful for the preparation of aminoalkynes from the corresponding chloroalkyne and its precursor alkynyl alcohol wherein the chloroalkyne is water insoluble and the amination agent, such as ammonia or methylamine, is water soluble. Processes for the amination of chloroalkynes have been described by both Michelotti et al. in U.S. Pat. No. 5,254,584 and Hennion et al. in *J. Am. Chem. Soc.*, 75, 1653 (1953); however, the use of a surfactant in such processes was not disclosed or suggested. Another method of preparing an aminoalkyne by reaction of the chloroalkyne with sodium amide in liquid ammonia also has been disclosed in *J. Org. Chem.*, 45, 4616 (1980); however, such processes are only viable on a laboratory scale and are not suitable as a large scale commercial process.

The process of the present invention comprises the steps of a. reacting an alkynyl alcohol with HCl to form a chloroalkyne, b. reacting said chloroalkyne with a water soluble amination agent in the presence of a surfactant to form an aminoalkyne and, optionally, c. purifying said aminoalkyne by distillation.

More specifically, the process of this invention comprises the steps of a. reacting an alkynyl alcohol of the formula

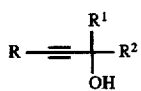

with an aqueous, saturated HCl solution to form a chloroalkyne of the formula

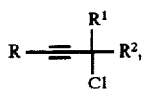

b. reacting said chloroalkyne with a water soluble amination agent of the formula $NR^3R^4$ in the presence of a non-ionic, cationic or amphoteric surfactant to form an aminoalkyne of the formula

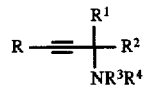

and, optionally, c. purifying said aminoalkyne by distillation;
wherein
R is a hydrogen atom, alkyl, cycloalkyl, cycloalkylalkyl or aralkyl;
$R^1$ and $R^2$ are each independently alkyl, cycloalkyl, cycloalkylalkyl, aralkyl or, together with the carbon atom to which they are attached, form cycloalkyl; and
$R^3$ and $R^4$ are each independently a hydrogen atom or a lower alkyl.

In this invention, alkyl is straight or branched chain ($C_1$–$C_8$)alkyl and includes, for example, methyl, ethyl, n-propyl, isopropyl, n-butyl, isobutyl, sec-butyl, tert-butyl, n-amyl, isoamyl, n-hexyl and n-octyl. Lower alkyl is straight or branched chain ($C_1$–$C_4$)alkyl. Cycloalkyl includes, for example, cyclopentyl and cyclohexyl. Cycloalkylalkyl includes, for example, cyclopentylmethyl, cyclohexylethyl, 3-cyclopentylpropyl, 4-cyclohexylbutyl and the like. For aralkyl, the aryl part of the moiety is defined as phenyl or phenyl substituted with one or two substituents independently selected from halo and alkyl; the alkyl part of the moiety is defined as straight chain ($C_1$–$C_4$)alkyl. Examples of aralkyl include benzyl, phenethyl, 4-chlorobenzyl, 4-methylbenzyl and 2-chlorophenethyl.

In a preferred embodiment of this invention, R is a hydrogen atom or lower alkyl. $R^1$ and $R^2$ are independently lower alkyl or, together with the carbon atom to which they are attached, form cyclopentyl or cyclohexyl. $R^3$ and $R^4$ are independently a hydrogen atom or lower alkyl, and the surfactant is non-ionic. In a more preferred embodiment of this invention, R is a hydrogen atom. $R^1$ and $R^2$ are independently methyl or ethyl. $R^3$ and $R^4$ are both hydrogen atoms, and the surfactant is an alkylphenoxy polyethoxy ethanol. In an even more preferred embodiment of this invention, $R^1$ is methyl and $R^2$ is methyl or ethyl.

The reaction sequence for both steps 1 and 2 is most conveniently carried out at ambient pressure and a temperature of from about 10° C. to about –10° C. However, if desired, the sequence can be run under pressure greater than atmospheric and at higher temperatures. The stoichiometry is relatively unimportant, but it is generally most convenient to employ a stoichiometric excess of HCl in the first step and a stoichiometric excess of amination agent in the second step. A chlorination catalyst such as copper (I) chloride may be utilized in the first step. A hydrogen chloride sink, for example, a strong base such as sodium or potassium hydroxide, is generally used in the second step to reduce consumption of the amination reagent; however, an excess of amination reagent can also be employed as the HCl sink if desired. The reaction times for both steps can vary and are usually dependent upon the cooling capacity and the mixing characteristics of the reaction vessel; conversion of starting material to the desired intermediate or product is conveniently followed using gas liquid chromatography (GLC) or high performance liquid chromatography (HPLC). The amount of surfactant utilized in step 2 can be varied but is generally within the range of 0.01–10% by weight based on the amount of organic chloride present. Preferably, the amount of surfactant will be within the range of 0.1–1.0% by weight based on the amount of organic chloride present.

The following examples are meant to further illustrate the present invention and are not limiting to its scope which is defined by the claims.

EXAMPLE 1:

Formation of 3-Chloro-3-Methyl-1-Pentyne

To a reactor, consisting of a 1-L resin kettle equipped with a thermometer, gas dispersion tube, overhead stirring motor with a retreat agitator blade, Lauda type circulating bath, caustic scrubber and a pressure equalizing addition funnel with attachment for a slow nitrogen sweep, was added 300 mL (3.6 mol) of concentrated hydrochloric acid along with 1.58 g (16 mmol) of copper (I) chloride. The cooling bath was set to 0° C., and hydrogen chloride gas was introduced. The dissolution of HCl was exothermic; as the solution approached saturation, the bath temperature was lowered further until a kettle temperature of —5° C. was reached. The 3-methyl-1-pentyn-3-ol (250 g, 2.5 mol) was charged to the addition funnel. A slow nitrogen sweep was started to keep the HCl vapor from reaching the alcohol through the side arm. The alcohol was added dropwise at a rate such that the reaction temperature remained at 0° C. or less for 2–3 hours. Addition of hydrogen chloride gas was continued during the feed to maintain saturation. At the end of the feed, the hydrogen chloride addition was stopped and the dispersion tube elevated above the level of the liquid. The reaction mixture was allowed to stir for 30 minutes at 0° C., then the agitation was stopped and the layers allowed to separate. The lower aqueous layer was drawn off and the organic phase was washed with water and then with a mixture of saturated brine and sodium bicarbonate solution. The organic phase was stored in a refrigerator until used for the next step. The procedure afforded about 280–290 g of a yellow to brown liquid whose estimated purity by GLC was found to be between 90–96%.

EXAMPLE 2:

Formation of 3-Amino-3-Methyl-1-Pentyne

To a reactor, consisting of a 1-liter resin kettle equipped with an overhead stir motor, Lauda type refrigerated bath, gas dispersion tube, two pressure equalizing addition funnels, thermometer, nitrogen sweep, and a gas inlet and exit equipped with the appropriate traps, was added 350 mL (2.6 mol) of concentrated ammonium hydroxide solution and 1.00 g of Triton® X-100 (Footnote 1). The cooling bath was set to approximately 0° C. and ammonia gas was introduced. The dissolution of ammonia was quite exothermic. As the solution approached saturation, the bath temperature was lowered further until a kettle temperature of —5° C. was reached. One of the addtion funnels was charged with 250 g (2.0 mol) of 3-chloro-3-methyl-1-pentyne and the other was charged with 172 g (2.2 mol) of 50% sodium hydroxide. A slow nitrogen sweep was placed on the chloride containing addition funnel to prevent ammonia vapors from entering the funnel through the side arm. The chloride and caustic were simultaneously added dropwise at a rate such that the reaction temperature remained at 0° C. or less for 3–4 hours. Addition of ammonia gas was continued during the feed to maintain saturation. At the end of the feed, ammonia addition was stopped and the gas dispersion tube elevated above the level of the liquid. The reaction mixture was allowed to stir at 0° C. until the level of unreacted chloride was found to be less than 1% by GLC. Agitation was stopped and the layers allowed to separate. The lower aqueous layer was dawn off and discarded and the upper organic layer was transferred to a distillation flask along with 75 mL of water. The mixture was then distilled using a 15 cm jacketed Vigreuex column. The fraction boiling between 85–92° C. was collected to afford 174.3 g of a water white liquid. The main fraction distilled as an azeotrope with water. This material was found to contain ~28% water. Of the remaining organic material, GLC analysis indicated 90% 3-amino-3-methyl-1-pentyne with most of the remainder being 3-methyl-1-pentyn-3-ol and butanone. The yield of 3-amino-3-methyl-1-pentyne was 60% based on the 3-chloro-3-methyl-1-pentyne starting material.

COMPARATIVE EXAMPLE

Formation of 3-Amino-3-Methyl-1-Pentyne

The procedure used was substantially similar to that employed in Example 2 except that no surfactant was added to the reactor system. The yield of 3-amino-3-methyl-1-pentyne in this case was 39% based on the 3-chloro-3-methyl-1-pentyne starting material.

It should be understood that the instant specification is set forth by way of illustration and not limitation, and that various modifications and changes can be made without departing from the spirit and scope of the present invention as defined by the appended claims.

We claim:

1. A process for the synthesis of an aminoalkyne which comprises the steps of
   a. reacting an alkynyl alcohol with HCl to form a chloroalkyne,
   b. reacting said chloroalkyne with a water soluble amination agent in the presence of a surfactant to form an aminoalkyne and, optionally,
   c. purifying said aminoalkyne by distillation.
2. The process of claim 1 which comprises the steps of
   a. reacting an alkynyl alcohol of the formula

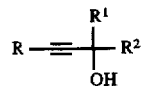

with an aqueous, saturated HCl solution to form a chloroalkyne of the formula

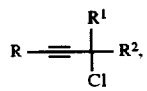

b. reacting said chloroalkyne with a water soluble amination agent of the formula $NR^3R^4$ in the presence of a non-ionic, cationic or amphoteric surfactant to form an aminoalkyne of the formula

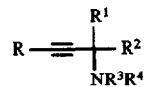

and, optionally, c. purifying said aminoalkyne by distillation;
wherein
R is a hydrogen atom, alkyl, cycloalkyl, cycloalkylalkyl or aralkyl;
$R^1$ and $R^2$ are each independently alkyl, cycloalkyl, cycloalkylalkyl, aralkyl or, together with the carbon atom to which they are attached, form cycloalkyl; and $R^3$ and $R^4$ are each independently a hydrogen atom or a lower alkyl.

3. The process of claim 2 wherein R is a hydrogen atom or lower alkyl.

4. The process of claim 2 wherein $R^1$ and $R^2$ are independently lower alkyl or, together with the carbon atom to which they are attached, form cyclopentyl or cyclohexyl.

5. The process of claim 2 wherein $R^3$ and $R^4$ are independently a hydrogen atom or lower alkyl.

6. The process of claim 2 wherein the surfactant is non-ionic.

7. The process of claim 3 wherein R is a hydrogen atom.

8. The process of claim 4 wherein $R^1$ and $R^2$ are independently methyl or ethyl.

9. The process of claim 5 wherein $R^3$ and $R^4$ are both hydrogen atoms.

10. The process of claim 8 wherein $R^1$ is methyl and $R^2$ is methyl or ethyl.

11. A process for the synthesis of an aminoalkyne from a chloroalkyne comprising reacting said chloroalkyne with a water soluble amination agent in the presence of a surfactant.

12. The process of claim 11 wherein the chloroalkyne having the formula

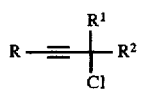

is reacted with a water soluble amination agent of the formula $NR^3R^4$ in the presence of a non-ionic, cationic or amphoteric surfactant to form an aminoalkyne of the formula

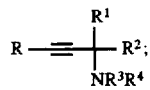

wherein

R is a hydrogen atom, alkyl, cycloalkyl, cycloalkylalkyl or aralkyl;

$R^1$ and $R^2$ are each independently alkyl, cycloalkyl, cycloalkylalkyl, aralkyl or, together with the carbon atom to which they are attached, form cycloalkyl; and $R^3$ and $R^4$ are each independently a hydrogen atom or a lower alkyl.

13. The process of claim 12 wherein R is a hydrogen atom or lower alkyl.

14. The process of claim 12 wherein $R^1$ and $R^2$ are independently lower alkyl or, together with the carbon atom to which they are attached, form cyclopentyl or cyclohexyl.

15. The process of claim 12 wherein $R^3$ and $R^4$ are independently a hydrogen atom or lower alkyl.

16. The process of claim 12 wherein the surfactant is non-ionic.

17. The process of claim 13 wherein R is a hydrogen atom.

18. The process of claim 14 wherein $R^1$ and $R^2$ are independently methyl or ethyl.

19. The process of claim 15 wherein $R^3$ and $R^4$ are both hydrogen atoms.

20. The process of claim 18 wherein $R^1$ is methyl and $R^2$ is methyl or ethyl.

21. The process of claim 6 wherein the surfactant is an alkylphenoxy polyethoxy ethanol.

22. The process of claim 16 wherein the surfactant is an alkylphenoxy polyethoxy ethanol.

* * * * *